United States Patent [19]

Vaillancourt

[11] Patent Number: 4,998,713
[45] Date of Patent: Mar. 12, 1991

[54] NEEDLE CONNECTOR

[76] Inventor: Vincent L. Vaillancourt, 14 Bunyan Dr., Livingston, N.J.

[21] Appl. No.: 463,243

[22] Filed: Jan. 10, 1990

[51] Int. Cl.⁵ .......................................... A61M 25/00
[52] U.S. Cl. ................................. 604/283; 604/411; 604/905
[58] Field of Search ............. 604/283, 284, 192, 86, 604/88, 411–415, 905

[56] References Cited

U.S. PATENT DOCUMENTS

3,976,073 8/1976 Quick et al. ...................... 604/414
4,005,710 2/1977 Zeddies et al. .................... 604/86
4,752,292 6/1988 Lopez et al. ................... 604/905 X
4,834,716 5/1989 Ogle .................................. 604/192

Primary Examiner—John D. Yasko
Attorney, Agent, or Firm—Kenyon & Kenyon

[57] ABSTRACT

The needle connector is made with a shielded connector which is slotted to slide over an arm of a Y-site connector. A needle within the shielded connector is able to pierce a rubber stopper or seal in the end of the Y-site connector. A rotatable ring on the shielded connector has a cam surface at the end edge which locks against the arm of the Y-site connector while biasing the seal of the Y-site connector into sealing engagement with the interior of the shielded connector. The needle may be fixed in place or may be removably mounted in place via a needle hub.

31 Claims, 4 Drawing Sheets

NEEDLE CONNECTOR

This invention relates to a needle connector. More particularly this invention relates to a needle connector for a Y-site connector.

As is known, one continuing problem in hospitals, clinics, and the like is the threat of cutting by needles, e.g. needle sticks, which are used to convey fluids for medication purposes In order to reduce the risk of a needle stick, a number of proposals have been described, for example, U.S. Pat. No. 4,752,292 describes a medical connector wherein a needle is contained in a recessed manner within a narrow cap member. In this construction, the cap member is designed to fit snugly over an entry port structure with the needle positioned to pierce a seal on the entry port structure when the cap member is seated in place.

Another structure is described in U.S. Pat. No. 4,511,359 wherein a needle connector assembly is composed of one connector half which receives a needle in recessed manner and a second connector half which contains a seal which can be pierced by the needle when the two halves are brought together.

Structures of the above type are readily used with tubes and tubing having a straight configuration. However, difficulties arise in adapting these connectors to a Y-site connector. As is known, Y-site connectors are generally made with a straight tubular portion and a hollow arm which extends laterally from the hollow portion. Where the Y-site connector is provided with a seal at the end of the tubular portion adjacent the lateral arm, difficulties may arise in securing a needle connector in place over the seal, should the lateral arm interfere with the needle connector. Accordingly, efforts have been made to provide a needle connector which can envelope the entire Y-site connector. To this end, one known connector has been provided with a tubular part in which a needle is recessed as well as a coaxially extending tubular part having a slot at one end for fitting over the arm of a Y-site neck. In use, the connector is mounted over the end of a Y-site connector with the needle piercing through a seal in the end of a tubular tubular portion of the Y-site connector. At the same time, the arm of the Y-site connector moves into the slot provided by the extending tubular part of the needle connector. After the arm passes into the slot, the needle connector can be turned on the Y-site connector to secure a lug on the tubular portion against the arm of the Y-site connector. However, since the interior of the needle connector is spaced from the exterior of the Y-site connector, the interior volume of the needle connector may become contaminated in time, particularly in the area surrounding the needle.

Accordingly, it is an object of the invention to provide a needle connector for a Y-site connector which is capable of maintaining a non-contaminated environment within a needle puncture area.

It is another object of the invention to provide a needle connector which can be mounted on as multiplicity of differently sized Y-site connectors.

It is another object of the invention to provide a tight seal of a needle connector on a Y-site connector.

It is another object of the invention to provide a needle connector of relatively simple construction for Y-site connectors.

It is another object of the invention to provide a needle connector which can be readily mounted over existing Y site connectors.

Briefly, the invention provides a needle connector constructed to provide a seal-tight fit with a Y-site connector. In one embodiment, the needle connector is composed of three components, i.e. a pair of tubular parts and a hollow needle. In another embodiment, the needle connector is composed of two components and cooperates with a removable needle assembly.

In the first embodiment, one tubular part forms a shielded connector which has a chamber at one end for receiving a Y-site connector, a slot for passage over an arm of the Y-site connector and a second chamber at an opposite end coaxial of the first chamber. In addition, the shielded connector has a conical portion sized to sealingingly engage with a seal at the end of a Y-site connector.

The needle is fixedly mounted in the shielded connector in axial alignment with the chambers in order to communicate these chambers with each other. In addition, the needle projects into the first chamber in order to pass through a seal at one end of a Y-site connector.

The second tubular part is in the form of a ring which is movably mounted on the first tubular part for example, being rotatably secured to the first tubular part in coaxial relation. This ring also has a slot for passage over the arm of the Y-site connector as well as a cam surface at an end edge for engaging the arm of the Y-site connector.

In this embodiment, the needle connector is slid over a Y-site connector with the slot of the shielded connector receiving the lateral arm of the Y-site connector. At this time, the needle pierces through the seal on the Y-site connector while the seal engages with the internal conical portion of the shielded connector. Next the ring is rotated on the shielded connector so as to bring the cam surface of the ring against the lateral arm of the Y-site connector. Continued rotation forces the arm, and thus the Y-site connector, further into the needle connector. This, in turn, causes the seal to further engage with the shielded connector about the environment of the needle.

The construction of the needle connector is such as to be mounted over differently sized Y-site connectors. In this respect, the shielded connector containing the recessed needle can be sized to sealingly engage with different diameters of seals located on the ends of a Y-site connector.

In the second embodiment, the needle is removeably mounted in the part which forms the shielded connector of the needle connector. This permits the needle to be changed from time to time, for example, each time a dose of medication is to be given to a patient. To this end, the needle is mounted in a needle hub which, in turn, is removeably mounted within the shielded connector part of the needle connector, for example in a threaded relation.

These and other objects and advantages of the invention will become more apparent from the following detailed description taken in conjunction with the accompanying drawings wherein.

Figure 1:
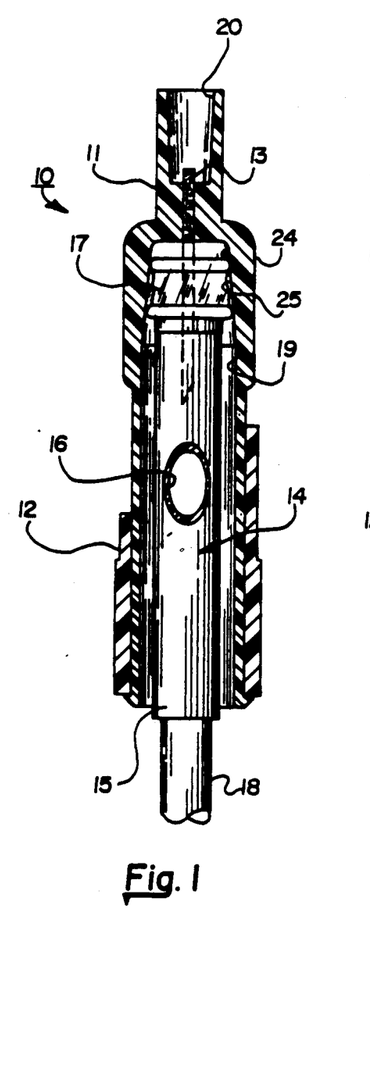
FIG. 1 illustrates a cross sectional view of the needle connector mounted in place on a Y-site connector in accordance with the invention.

Referring to FIG. 1, the needle connector 10 is composed of three parts, i.e. a pair of telescoping tubular parts 11, 12 and a needle 13. As indicated, the needle connector 10 is sized for mounting a Y-site connector 14 which includes a straight tubular portion 15 and an arm 16 which extends laterally from the tubular portion 15. As indicated, the tubular portion 15 also carries a seal 17 at one end for closing off the tubular portion 15. The opposite end receives a tubing 18 which extends, for example to an intravenous line (not shown) The Y-site connector 14 is of conventional construction and need not be further described.

Figure 2:
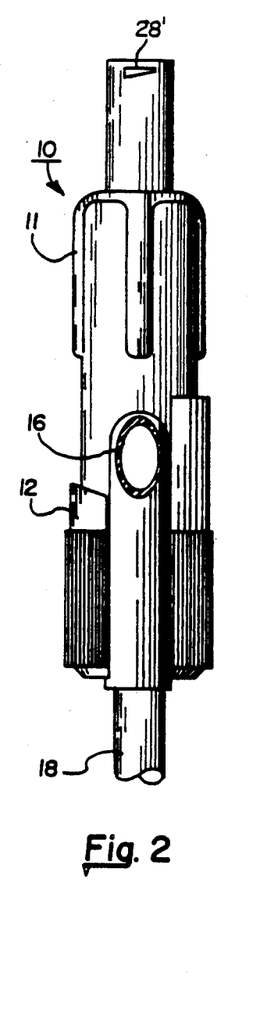
FIG. 2 illustrates a front view of a needle connector mounted on a Y-site connector in accordance with the invention.
Figure 3:
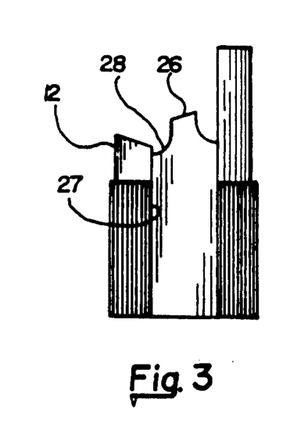
FIG. 3 illustrates an exploded view of the needle connector of FIG. 1.

Referring to FIGS. 2 and 3, the upper tubular part 11 of the needle connector 10 forms a shielded connector 11 of tubular shape and has a chamber 19 for receiving the tubular portion 15 of the Y-site connector 14 as well as a second chamber 20 at the upper end, as viewed, for receiving, for example, a syringe or other means for supplying a fluid. The needle 13 is hollow so as to communicate the chambers 20, 19 with each other for the passage of a fluid therebetween.

Referring to FIG. 3, the shielded connector 11 also has an axial slot 21 which is sized for passage over the arm 16 of the Y-site connector 14. In addition, a peripheral bead or rim 22 is provided on the end of the shielded connector 11 while the Other tubular part 12 which is in the form of a ring has an annular groove 23 for receiving the rim 22 in snap-fit relation The bead 22 and groove 23 serve to form a snap-fit arrangement for locking the tubular parts 11, 12 together in freely rotatable relation to each other about a common axis.

The shielded connector 11 also has a conical portion 24 which provides an internal conical surface 25 for sealing engagement with the seal 17.

The ring 12 functions as a locking ring and has a cam surface 26 at an end edge as well as an axial slot 27 which extends over the entire length of the ring 12. In addition, a plurality of depressions 28 are provided along the cam surface 26.

Referring to FIG. 2, in use, the slots 21, 27 of the tubular parts 11, 12 of the needle connector 10 are aligned. Thereafter, the needle connector 10 is slid over the end of the Y-site connector 14 with the arm 16 passing first through the slot 27 of the ring 12 and then into the slot 21 of the shielded connector 11. During this time, the needle 13 pierces through the seal 17 into communication with the interior of the Y-site connector tubular portion 15 as indicated in FIG. 1.

After the arm 16 passes through the slot 27 of the ring 12, the ring 12 is rotated so as to bring a depression 28 into alignment with the arm 16 so as to lock the needle connector 10 to the Y-site connector 14.

In the event that the needle connector 10 is mounted on a differently sized Y-site connector 14, the ring 12 can be rotated more or less so as to force the arm 16 of the Y-site connector in a direction towards the needle 13 so as to increase the force sealing the seal 17 against the conical surface 25 within the shielded connector 11. To this end, the cam surface 26 may be provided with a multiplicity of depressions or detents 28 in Which the arm 16 can be seated in order to lock the needle connector 10 to the Y-site connector 14.

The seal-tight fit of the seal 17 of the Y-site connector 14 in the shielded connector 11 prevents contamination of the space surrounding the needle 13 during use.

After mounting in place, a suitable supply means may be connected to the remaining chamber 20 of the needle connector 10 so as to infuse fluid into the Y-site connector 14, for example, a syringe may be releaseably secured to the end of the needle connector 10 via ears 28' on the outer surface of the shielded connector.

Figure 4:
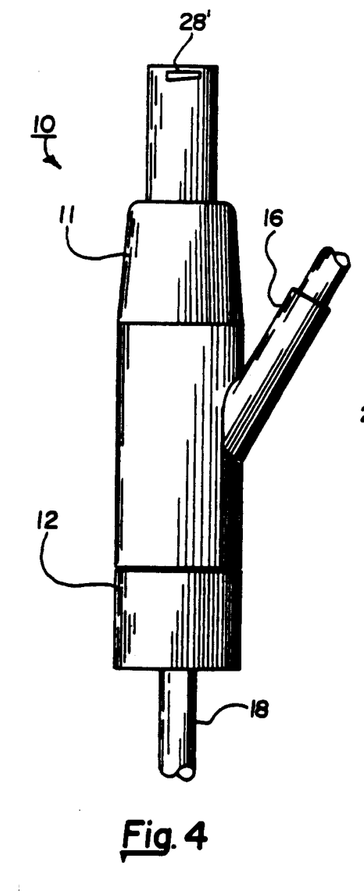
FIG. 4 illustrates a perspective view of a modified needle connector mounted on a Y-site connector in accordance with the invention.
Figures 5, 6:
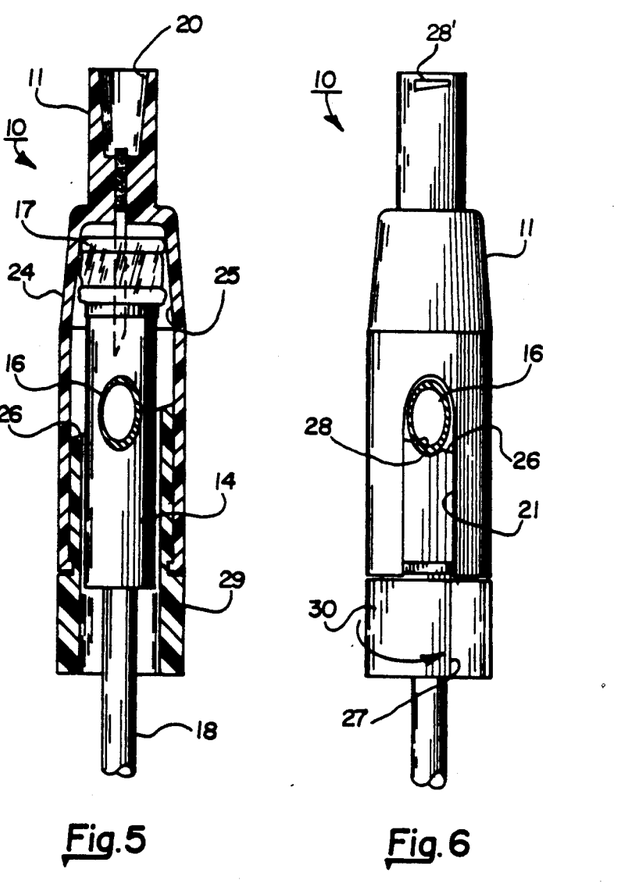
FIG. 5 illustrates a cross sectional view of the needle connector of FIG. 4.
FIG. 6 illustrates a front view of the needle connector of FIG. 4.

Referring to FIGS. 4 to 6, wherein like reference characters indicate like parts as above, the needle connector 10' may be constructed with the telescoping parts 11, 12 in reverse order. That is, the ring 12 may be disposed to rotate within the shielded connector 11. In addition, the ring 12 may be provided with an enlarged shoulder portion 29 having an outer diameter equal to or substantially equal to the outer diameter of the shielded connector 11. In addition, this enlarged part 29 may be provided with a knurled surface 30 (see FIG. 6).

Figures 7, 8:
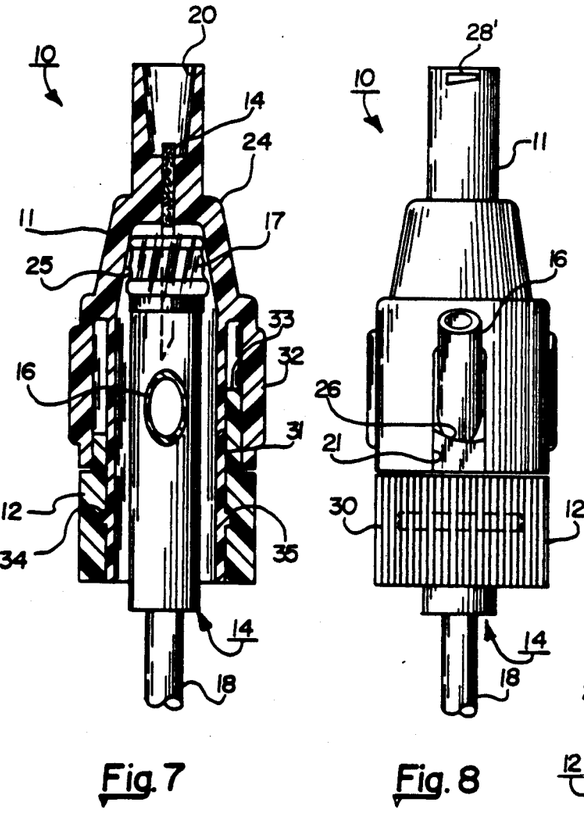
FIG. 7 illustrates a cross-sectional view of a further modified needle connector constructed in accordance with the invention.
FIG. 8 illustrates a front View of the needle connector of FIG. 7 in place.
Figure 9:
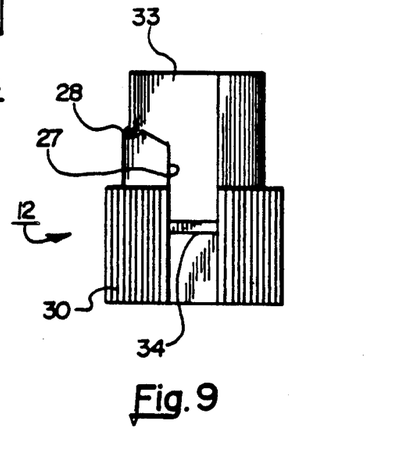
FIG. 9 illustrates a view of a ring of the needle connector of FIG. 8.
Figure 10:
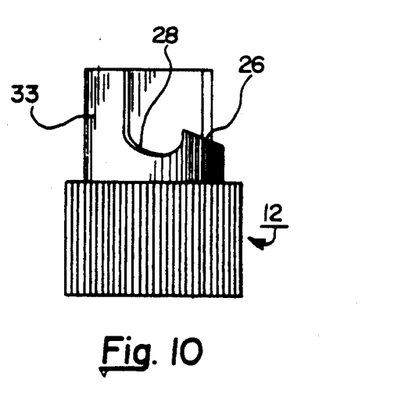
FIG. 10 illustrates a view of the ring of FIG. 9 rotated 90°.

Referring to FIGS. 7 and 8, wherein like reference characters indicate like parts as above, the needle connector 10 may alternatively be made such that the shielded connector 11 has a tubular skirt 31 and a tubular wall 32 disposed in concentric relation to each other and in spaced apart relation so as to receiVe a sleeve-like portion 33 of the ring 12". As shown in FIGS. 9 and 10, the skirt 31 is provided with a peripheral bead 34 while the ring 12 is provided with an internal groove 35 to receive the bead 34 in locking relation to prevent axial displacement between the components while permitting rotation of the components 11, 12 relative to each other.

In this embodiment, placement of the sleeve portion 33 of the ring 12 between the skirt 31 and wall 32 stiffens the sleeve portion. Since the ring 12 is disposed outside the skirt 31, there is no relative movement, i.e. sliding, of the ring 12 on the tubular portion 15 of the Y-site connector 14. The trapping of the sleeve portion 33 also prevents the slotted sleeve portion 33 from flaring outwardly.

Figure 11:
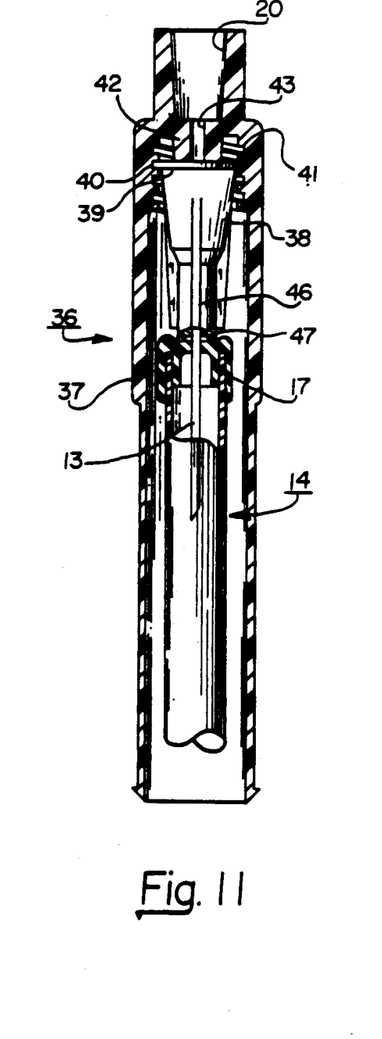
FIG. 11 illustrates a cross-sectional view of a o modified needle connector constructed in accordance with the invention.

Referring to FIG. 11, wherein like reference characters indicate like parts as above, the needle connector 36 may be constructed of two parts, i.e. a tubular part (shielded connector) 37 and a ring (not shown) similar to that described above while the needle 13 is removeably mounted within the connector 36. To this end, the needle 13 is mounted in a needle hub 38 to form an assembly which is removeably mounted within the shielded connector 37.

As indicated, the needle hub 38 is of generally conventional structure and is sized so as to be fitted within the shielded connector 37. For example, the needle hub 38 carries a collar 39 at one end from which a pair of ears 40 project so as to threadably engage with an internal thread 41 on the anterior wall of the shielded connector 37.

In order to communicate the chamber 20 with the hollow needle 13, a male luer type connection 42 is provided within the shielded connector 37 to provide a passage 43 communicating the chamber 20 with the hollow needle 13. In this respect, upon insertion of a syringe (not shown) into the chamber 20, a dose of medication or other fluid may then be dispensed through the male luer type connection 42 into and through the hollow needle 13 into a Y-site connector 14 inserted within the needle connector 36.

Figures 12, 13:
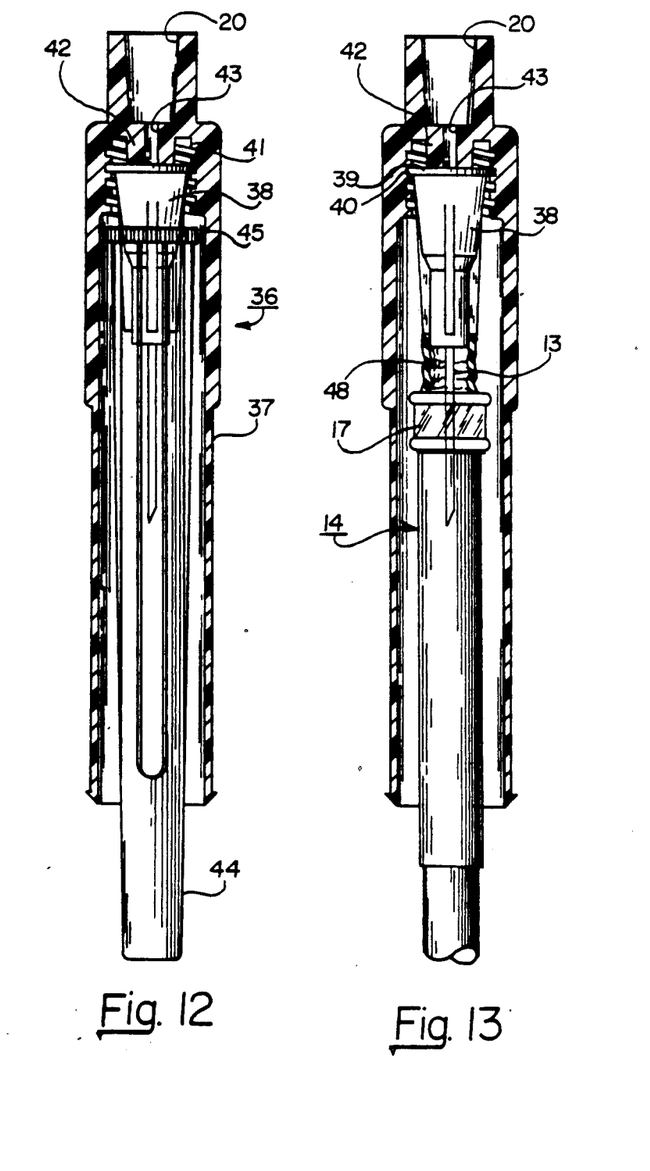
FIG. 12 illustrates a view of the needle connector of FIG. 11 during removal of a needle hub and needle assembly.
FIG. 13 illustrates a further modified needle connector constructed in accordance with the invention.

Referring to FIG. 12, in order to remove the needle hub 38, a transparent tube 44 or the like is inserted into the needle connector 37 to engage over the outer circumference of the needle hub 38. In this respect, the tube 44 carries a flange 45 at the end which may be provided with internal notches (not shown) to engage with ribs 46 extending longitudinally along the needle hub 38. After interengagement of the ribs 46, the tube 44 can be turned so the needle hub 38 is unthreaded from the thread 41 of the shielded connector 37 and then removed. Insertion of a fresh needle hub 38 with a needle 37 is effected in a reverse manner.

Referring to FIG. 11, when a Y-site connector 14 is s inserted into the shielded connector 37, the seal 17 at the end of the Y-site connector 14 is brought into abutment with the distal end of the needle hub 38. In order to effect a seal about the needle 13, the needle hub 38 is provided with a depending annular skirt 47 about the needle 13 which penetrates slightly into the seal 17 to maintain an effective seal about the needle 13.

In this embodiment, a seal may not be effected when the needle 13 penetrates the rubber seal 17. In this case, When a removable needle is used, the needle 13 may be changed prior to each medication at the discretion of the hospital or the entity administrating the medication. In this way, the potential effect of having a contaminated area immediately adjacent to the penetrating needle 13 is eliminated and there is no need for a non-contaminated zone. In this case, the needle is removed and exchanged for a fresh sterile one. In addition, the rubber surface of the seal 17 is cleaned with an antiseptic, such as povidone iodine, prior to reinsertion of a sterile needle.

Depending upon the length of the needle hub 38, the ring (not shown) of the needle connector 36 is rotated more or less so as to cause engagement of the seal 17 of the Y-site connector 14 against the needle hub 38. To this end, the cam surface of the ring may be suitably shaped to effect a different amount of movement of the needle connector 36 over the Y-site connector 14 from one recess of the cam surface to the next recess.

Referring to FIG. 13, wherein like reference characters indicate like parts as above, a needle hub 38 may be provided with a resiliently collapsible ring or sleeve 48, for example of rubber in order to effect a seal about the needle 13 when the needle connector 36 is fitted over a Y-site connector 14. As illustrated, such a sleeve 48 would be able to collapse to different degrees between the needle hub 38 and the seal 17 depending upon the amount of penetration of the Y-site connector 14 into the needle connector 10.

In each of the above embodiments, the ring is attached to the shielded connector in such a fashion as to be free to rotate around the axis of the connector. After the arm of Y-site connector 14 is captured within the shielded connector slot 21, the ring 12 can be rotated to progressively close the slot 21 and engage the arm 16. The action of the ring 12 is positive and can readily achieve a good tight fit.

The invention thus provides a needle connector which can be readily mounted on all types of extending Y-site connectors while achieving a secure seal about the needle of the needle connector to prevent contamination.

Further, the invention provides a needle connector of relatively simple construction which can be readily manipulated and locked in place on a Y-site connector.

What is claimed is:

1. A needle connector for mounting on a Y-site connector, said needle connector including
    a first tubular part having a first chamber at one end for receiving a hollow needle, a second chamber at an opposite end coaxial of said first chamber for communication therewith, and an axial slot at said one end for passage of an arm of a Y-site connector therethrough; and
    a second tubular part rotatably secured to said first tubular part in coaxial relation for fitting over a Y-site connector, said second part having an axial slot for passage of the arm of the Y-site connector and a surface for engaging the Y-site connector arm to bias the Y-site connector into said first part towards a needle therein in response to rotation of said second part relative to said first part.

2. A needle connector as set forth in claim 1 wherein said second part is rotatably mounted concentrically about said first part.

3. A needle connector as set forth in claim 1 wherein said second part is rotatably mounted concentrically within said first part.

4. A needle connector as set forth in claim 1 wherein said first part has a peripheral rim at one end and said second part has a peripheral groove receiving said rim in locking relation.

5. A needle connector as set forth in claim 1 wherein said cam surface includes an arcuate depression for releaseably receiving the arm of the Y-site connector.

6. A needle connector as set forth in claim 1 wherein said first part includes a tubular skirt and a + wall coaxially of and spaced from said skirt to slidably receive said second part therebetween.

7. A needle connector as set forth in claim 6 wherein said skirt has a peripheral rim and said second part has a peripheral groove receiving said rim in locking relation.

8. A needle connector as set forth in claim 1 wherein said cam surface is disposed on an end edge of said second part.

9. A needle connector as set forth in claim 1 which further comprises a hollow needle fixedly mounted in said first part.

10. A needle connector as set forth in claim 1 which further comprises a needle removably mounted in said first part.

11. A needle connector as set forth in claim 10 which further comprises a needle hub removably mounted within said first part and having said needle secured therein.

12. A needle connector as set forth in claim 11 wherein said first part has an internal thread and said needle hub has a plurality of projecting ears threadably engaging said thread to retain said needle hub in said first part.

13. In combination
    a Y-site connector having a tube and a hollow arm extending laterally from said tube;
    a seal at one end of said tube; and
    a needle connector having a first part enveloping said one end of said tube, a hollow needle facing said seal and a second part movably mounted relative to said first part and having a surface for engaging said arm to move said Y-site connector relative to said needle during piercing of said needle through said seal.

14. The combination as set forth in claim 13 wherein each said part has a slot for passage over said arm.

15. The combination as set forth in claim 13 wherein said second part is rotatably mounted relative to said first part and said surface is a cam surface on an end of said second part.

16. The combination as set forth in claim 15 wherein said cam surface includes an arcuate depression for releaseably receiving said arm of said Y-site connector.

17. The combination as set forth in claim 13 wherein said first part has a peripheral rim at one end and said second part has a peripheral groove receiving said rim in locking relation.

18. The combination as set forth in claim 13 wherein said first part includes a tubular skirt and a tubular wall coaxially of and spaced from said skirt to slidably receive said second part therebetween.

19. The combination as set forth in claim 18 wherein each of said skirt and said wall has an axial slot for passage over said arm.

20. The combination as set forth in claim 13 wherein said seal sealingly engages with said first part upon passage of said needle through said seal.

21. The combination as set forth in claim 20 wherein said first par has a conical portion sized to sealingly engage with said seal.

22. The combination as set forth in claim 13 which further comprises a needle hub releaseably secured in said first part and having said needle secured therein.

23. The combination as set forth in claim 22 wherein said first part has a chamber at one end remote from said Y-site connector and in communication with said needle for receiving a syringe for the injection of fluid into said tube of said Y-site connector.

24. The combination as set forth in claim 22 which further comprises a resilient collapsible annular seal about said needle and between said hub and said Y-site connector.

25. In combination
    a Y-site connector having a tube defining a passage of a fluid flow and a hollow arm extending from said tube and being in communication with said passage;
    a seal disposed in one end of said tube;
    a needle connector mounted on and about said arm of said Y-site connector, said needle connector including a shielded connector receiving said tube coaxially therein and having a slot receiving said arm, a hollow needle aligned with and facing said seal, a chamber communicating with said needle on a side opposite said seal and a mounted ring rotatably relative to said shielded connector and having a slot receiving said arm and a surface for engaging said arm to move said Y-site connector relative to said needle.

26. The combination as set forth in claim 25 wherein said surface is a cam surface on an end of said ring at least one arcuate depression for releaseably receiving the arm of the Y-site connector.

27. The combination as set forth in claim 25 wherein said shielded connector has a peripheral rim at one end and said has a peripheral groove receiving said rim in locking relation.

28. The combination as set forth in claim 25 wherein said shielded connector includes a tubular skirt and a tubular wall coaxially of and spaced from said skirt, and said ring has a sleeve-like portion slidably received between said skirt and said wall.

29. The combination as set forth in claim 25 wherein said shielded connector has a conical portion sized to sealingly engage with said seal and said seal sealingly engages with said shielded connector upon passage of said needle through said seal.

30. The combination as set forth in claim 25 which further comprises a needle hub releaseably secured in said shielded connector with said needle secured therein 31. The combination as set forth in claim 30 wherein said seal sealingly engages with said needle hub upon passage of said needle through said seal.

* * * * *

UNITED STATES PATENT AND TRADEMARK OFFICE
CERTIFICATE OF CORRECTION

PATENT NO. : 4,998,713

DATED : March 12, 1991

INVENTOR(S) : VINCENT L. VAILLANCOURT

It is certified that error appears in the above-identified patent and that said Letters Patent is hereby corrected as shown below:

```
Column 1, line 62 change "as" to -a-
Column 3, line 13 change "View" to -view-
Column 3, line 19 change "a o modi" to -a modi- -
Column 3, lines 52-55 delete "while .... arrangement"
Column 4, line 18 change "Which" to -which-
Column 4, line 32 change "10'" to -10-
Column 4, line 47 change "12" " to -12-
Column 4, line 46 change "receiVe" to -receive-
Column 5, line 10 change "With" to -with-
Column 5, line 42 change "When" to -when-
Column 6, line 48 delete "cam"
Column 6, line 51 change "t" to -tubular-
```

UNITED STATES PATENT AND TRADEMARK OFFICE
CERTIFICATE OF CORRECTION

PATENT NO. : 4,998,713

DATED : March 12, 1991

INVENTOR(S) : VINCENT L. VAILLANCOURT

Page 2 of 2

It is certified that error appears in the above-identified patent and that said Letters Patent is hereby corrected as shown below:

```
Column 6, line 55 change "rim" to -bead-
Column 6, line 56 change "rim" to -bead-
Column 6, line 59 delete "cam"
Column 7, line 43 change "par" to -part-
Column 8, line 20 change "mounted ring rotatably" to - ring
     rotatably mounted-
Column 8, line 26 after "ring" insert -including-
Column 8, line 31 after "and said" insert -ring-
```

Signed and Sealed this

Sixth Day of October, 1992

*Attest:*

DOUGLAS B. COMER

*Attesting Officer*        *Acting Commissioner of Patents and Trademarks*